United States Patent
Hoeck et al.

(10) Patent No.: US 6,585,690 B1
(45) Date of Patent: Jul. 1, 2003

(54) HYPODERMIC SYRINGE WITH SELECTIVITY RETRACTABLE NEEDLE

(75) Inventors: Roger Hoeck, Holdrege, NE (US); Charles L. Bush, Jr., Fairfield, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 146 days.

(21) Appl. No.: 09/606,743

(22) Filed: Jun. 29, 2000

(51) Int. Cl.⁷ .............................................. A61M 5/00
(52) U.S. Cl. ..................... 604/110; 604/218; 604/135; 604/198
(58) Field of Search ................. 604/110, 218, 604/195, 198, 181, 187, 192, 203, 205, 206, 223, 225, 226, 228, 229, 235

(56) References Cited

U.S. PATENT DOCUMENTS

| | | |
|---|---|---|
| 4,233,975 A | 11/1980 | Yerman |
| 4,838,863 A | 6/1989 | Allard et al. |
| 4,838,869 A | 6/1989 | Allard |
| 4,900,307 A | 2/1990 | Kulli |
| 4,927,414 A | 5/1990 | Kulli |
| 4,929,237 A | 5/1990 | Medway |
| 4,946,446 A | 8/1990 | Vadher |
| 4,955,870 A | 9/1990 | Ridderheim et al. |
| 4,966,593 A | 10/1990 | Lennox |
| 4,973,316 A | 11/1990 | Dysarz |
| 4,994,034 A | 2/1991 | Botich et al. |
| 5,011,476 A | 4/1991 | Foster |
| 5,013,301 A | 5/1991 | Marotta, Jr, et al. |
| 5,019,044 A | 5/1991 | Tsao |
| 5,045,063 A | 9/1991 | Spielberg |
| 5,046,508 A | 9/1991 | Weissler |
| 5,047,017 A | 9/1991 | Koska |
| 5,049,133 A | 9/1991 | Villen Pascual ............ 604/110 |

(List continued on next page.)

*Primary Examiner*—Teresa Walberg
*Assistant Examiner*—Vinod D. Patel
(74) *Attorney, Agent, or Firm*—Jeanne P. Lukasavage (57) ABSTRACT

A hypodermic syringe with a selectively retractable needle includes an elongate barrel defining a receiver and a hollow bore. The syringe has a plunger with an elongate cavity open to the proximal end. The plunger is sized to fit within the bore of the barrel for a slidable movement to define a chamber for receiving and expelling fluids. The inside diameter of the cavity in the plunger is sufficient to accept telescopically at least a part of a first portion of the plunger. A second portion and the first portion are joined at an attachment to form a shoulder extending outwardly from the first portion, with the plunger being telescopically collapsible by movement of the second portion into the cavity by of sufficient distal force to frangibly disrupt the attachment. The syringe includes an elongate sleeve sized to fit over the first portion of the plunger and extend from the shoulder. The plunger includes a stopper to a form fluid tight seal with the barrel. The sleeve has a cutting surface inside of the stopper. The syringe includes a hub with a proximal flange and a passageway within the receiver. The syringe has a needle with a pointed distal end mounted in the passageway of the hub extending distally outwardly. When sufficient distal force is applied to collapse the plunger, the cutting surface of the sleeve cuts through the stopper and through the flange of the hub and releases it from the receiver to retract the needle.

21 Claims, 8 Drawing Sheets

U.S. PATENT DOCUMENTS

| | | |
|---|---|---|
| 5,053,010 A | 10/1991 | McGary et al. |
| 5,064,419 A | 11/1991 | Gaarde |
| 5,084,018 A | 1/1992 | Tsao |
| 5,084,029 A | 1/1992 | Tagliaferri et al. |
| 5,085,640 A | 2/1992 | Gibbs |
| 5,092,853 A | 3/1992 | Couvertier, II |
| 5,114,410 A | 5/1992 | Caralt Batlle |
| 5,180,369 A | 1/1993 | Dysarz |
| 5,180,370 A | 1/1993 | Giillespie |
| 5,188,599 A | 2/1993 | Botich et al. |
| 5,201,710 A | 4/1993 | Caselli |
| 5,211,629 A | 5/1993 | Pressly et al. |
| 5,232,447 A | 8/1993 | Schwarz et al. |
| 5,232,456 A | 8/1993 | Gonzalez |
| 5,267,961 A | 12/1993 | Shaw |
| 5,267,976 A | 12/1993 | Guerineau et al. |
| 5,342,308 A | 8/1994 | Boschetti |
| 5,376,080 A | 12/1994 | Petrussa |
| 5,385,551 A | 1/1995 | Shaw |
| 5,389,076 A | 2/1995 | Shaw |
| 5,395,337 A | 3/1995 | Clemens et al. |
| 5,407,431 A | 4/1995 | Botich et al. |
| 5,407,436 A | 4/1995 | Toft et al. |
| 5,423,758 A | 6/1995 | Shaw |
| 5,487,732 A | 1/1996 | Jeffrey |
| 5,531,694 A | 7/1996 | Clemens et al. |
| 5,542,927 A | 8/1996 | Thorne et al. |
| 5,562,629 A | 10/1996 | Haughton et al. |
| 5,573,510 A | 11/1996 | Isaacson |
| 5,575,777 A | 11/1996 | Cover et al. |
| 5,578,011 A | 11/1996 | Shaw |
| 5,605,544 A | 2/1997 | Tsao |
| 5,613,952 A | 3/1997 | Pressly, Sr. et al. |
| 5,632,733 A | 5/1997 | Shaw |
| 5,634,909 A | 6/1997 | Schmitz |
| 5,637,092 A | 6/1997 | Shaw |
| 5,643,211 A | 7/1997 | Sadowski et al. |
| 5,681,292 A | 10/1997 | Tober et al. |
| 5,685,863 A | 11/1997 | Botich et al. |
| 5,769,822 A | 6/1998 | McGary et al. ............ 604/110 |
| 5,782,804 A | 7/1998 | McMahon |
| 5,788,677 A | 8/1998 | Botich et al. |
| 5,792,107 A | 8/1998 | Petrocelli |
| 5,800,395 A | 9/1998 | Botich et al. |
| 5,800,403 A | 9/1998 | Pressly, Sr. et al. |
| 5,853,390 A | 12/1998 | Freschi |
| 5,882,342 A | 3/1999 | Cooper et al. |
| 5,885,257 A | 3/1999 | Badger |
| 5,935,104 A | 8/1999 | Janek et al. |
| 5,984,898 A | 11/1999 | Garvin |
| 6,004,278 A | 12/1999 | Botich et al. |
| 6,010,486 A | 1/2000 | Carter et al. ............... 604/195 |
| 6,368,303 B1 * | 4/2002 | Caizza ...................... 604/110 |

\* cited by examiner

HYPODERMIC SYRINGE WITH SELECTIVITY RETRACTABLE NEEDLE

FIELD OF INVENTION

The present invention is generally related to hypodermic syringes and more particularly to syringes that include a needle that is retractable after the intended use to substantially prevent inadvertent exposure to the needle and reuse of the syringe.

BACKGROUND

Hypodermic syringes are widely used in the medical arts for administering medicaments and for drawing body fluid samples. Generally, hypodermic syringes have a metal needle attached either fixedly or removably that has a sharpened distal point for penetrating vial stoppers or patient's skin. The hypodermic syringes and needles have been used for many years with few problems reported when the vast numbers and needles being used are considered. More recently, with the recognition of viral diseases that are transmitted by body fluids and greater sensitivity of the need to protect health care workers from inadvertent contact with previously used needles (commonly referred to as "sharps") as well as the need to reduce criminal misuse of improperly disposed of needles and syringes, syringes and needles that include provisions to prevent reuse have been developed.

Provisions intended to prevent reuse of needles and syringes include a variety of sharps collector systems that are widely used in health care facilities. Other developments include needle attachments that may be readily broken off by practitioners once the syringe has completed its intended use. A variety of shielding mechanisms has been developed; some of which are currently commercially available. While many of these developments have reduced the incidence of inadvertent exposure of healthcare workers to sharps, most of these devices can readily be overcome by an individual determined to obtain and misuse a hypodermic syringe and needle. As a result of this problem, further developments in the art of hypodermic syringes have resulted in syringes with needles that withdraw into the body of the syringe once their intended use is completed.

U.S. Pat. No. 4,838,869 discloses a retractable hypodermic needle configured for one time use wherein the needle is spring loaded and automatically irretrievably retracted into the hypodermic syringe when the syringe plunger is fully depressed, whereby protrusions on the end of the plunger engage tabs holding the spring loaded needle to release the needle for retraction. A potential problem with the design disclosed in this patent is that many times a practitioner may draw and expel a fluid several times during preparation for administration of a medicament, with this design, the practitioner could inadvertently discharge the retraction mechanism. Further, the design would be very difficult to manufacture in large volumes.

U.S. Pat. No. 4,900,307 discloses a hypodermic needle with an enlarged hub that provides provisions for selectively withdrawing the needle into the hub once the syringe and needle have completed their intended usage. While this disclosed design does substantially eliminate the problem of premature discharge of the retraction mechanism, the enlarged hub has a considerable "dead volume" that would result in a significant undeliverable retention of the medicament. Additionally, although the needle is secured in the hub after discharge, the syringe itself is still fully functional after the hub with the needle inside is removed.

U.S. Pat. No. 4,994,034 discloses a hypodermic injection system with a retractable needle wherein the needle retracts within the interior cavity of a syringe plunger. The disclosed invention includes a cylindrical spring housing with resilient fingers which capture a coiled spring that biasly holds a needle holder against the retaining force of the resilient fingers. The plunger in this disclosure has a frangible end, which when engaging the resilient fingers under a predetermined amount of force, dissociate which remaining inwardly-tapered shoulders spread the resilient fingers, allowing the coiled spring to eject the needle and its holder into the interior cavity of the syringe plunger. A syringe manufactured using this disclosure would be complex and difficult to assemble. It is believed that no successful commercial product has been produced using this disclosure.

U.S. Pat. No. 5,019,044 discloses a safety hypodermic syringe with a hypodermic needle fixed connected to a holder plate and constantly supported by a spring for making axial movement. The holder plate is normally retained by a clamp at a ready position for injection. When the plunger of the syringe is pushed to the bottom of the barrel, the needle is released from the clamp and is pushed by the spring to drop and further follow a rubber plug to be squeezed into a chamber in the plunger. Again, no successful commercial product has resulted from this disclosure, which would be complex to manufacture and appears to have a considerable undeliverable dead volume.

Another example of a syringe with a retractable needle is disclosed in U.S. Pat. No. 5,053,010. The disclosed syringe retracts the needle into a hollow plunger additional pressure on the plunger after the contents of the syringe are expelled. The disclosed design incorporates a sliding elastomeric seal which displaces from its forward position to a retracted position, thereby allowing additional forward travel of the plunger to actuate the retraction mechanism. A problem reported with this design is that, because of the soft nature of the seal, the seal may be prematurely displaced during its use in an injection. Attempts to overcome this difficulty by increasing the stiffness of the sealing member could impair the seal integrity.

U.S. Pat. No. 5,180,369 discloses a self destructive syringe assembly having a needle cannula fixed to a slidable piston. The slidable piston and slidable piston flange are held within the barrel of the syringe assembly by a compressed spring, a guide tube and a shatter ring. The plunger of the syringe assembly is a hollow elongated tube with a thumb flat at one end, a sliding gasket, a plunger shatter plate and a hook rim at the other end. The patent reports that when medicament is injected, the elongated hollow plunger is further thrust into the shatter ring, the shatter ring shatters, further allowing the slidable piston and slidable piston flange to thrust into the plunger shatter plate to shatter. The shattering of the plunger shatter plate causes the slidable piston and needle cannula to be thrust into the hollow plunger by the spring and is thus prevented from re-entering the guide tube. Again, no successful commercial product has resulted from this disclosure.

U.S. Pat. No. 5,180,370 discloses a syringe which has an internal mechanism for retracting the needle into the syringe after the injection has been given. In one disclosed embodiment, the needle is manually retracted by pulling back on the plunger, and in another, the needle is propelled by a compressed spring into a hollow chamber within the plunger. A syringe produced with this disclosure would be complex to manufacture, and no successful commercial product has resulted from this disclosure.

U.S. Pat. No. 5,188,599 discloses a hypodermic injection system with a needle that retracts within an interior cavity of the syringe plunger. The needle when retracted is held within the plunger. The disclosed device includes a cylindrical spring housing that has resilient fingers which capture a spring under bias holding a needle holder against the retaining force of resilient fingers. The plunger has a frangible end which dissociates when the outwardly tapered shoulders spread the resilient fingers, allowing the coiled spring to eject the needle and its holder into the interior cavity of the syringe plunger. The patent also discloses a body fluid sampling device that includes a double-ended needle for communication with an evacuated blood collection tube. This patent also includes a review of several earlier disclosures related to retractable needles. Attempts have been made to produce commercial products based on the disclosures of this patent, but as yet there is no successful commercial product.

U.S. Pat. No. 5,201,710 discloses a syringe fitted with a clamping device for the needle and with a mechanism to enable the needle to be automatically retractable into the syringe body at the end of an injection. The disclosed device includes inner and outer cylinders, openings at the ends of the outer cylinder, a third opening at an end of the inner cylinder and a closure for the third opening. The disclosed device further includes a needle with a head, a seal, a first spring to push the needle against the closure and a clamping device loaded by a second spring to maintain outward to the syringe and to release the needle. There is a diaphragm in the closure that bends before breaking and a sharp element to break the diaphragm. There also is a closure to prevent the needle from being accessible and a stop to prevent the second cylinder from being moved outwardly after the syringe is used. As is apparent from the description, the device disclosed by this patent is complex and would be difficult to assemble. No successful commercial product has resulted from the disclosure in this patent.

U.S. Pat. No. 5,385,551 discloses a non-reusable medical device that has a needle which is retractable by depression a plunger slidably mounted in the device. The disclosed device includes a front-mounted retraction mechanism that has a needle holder connected to the needle. The needle holder is supported along the axis of the device by a frictionally engaged retainer ring member coupled to the needle holder along an axially aligned sliding interface. The needle holder and retainer are positioned in the front portion of a hollow body. The front of a movable member or plunger presses against the retainer member passing around the needle holder which cannot move forward, thereby separating the retainer from the needle holder. The separation occurs by gradually reducing the extent of the sliding interface area until the retainer member pops loose from the needle holder whereupon the needle holder and needle are retracted into a cavity in the plunger in response to a retraction force applied to the needle holder by a previously compressed spring. Again, the device disclosed in this patent is complex, difficult to manufacture and appears to have significant undeliverable dead volume. Attempts have been made to commercialize products from this disclosure with only limited success.

U.S. Pat. No. 5,407,436 discloses a hypodermic syringe that has a hollow needle that is automatically retractable after use. The disclosed syringe includes a one-piece body molding has a main chamber for a plunger, sample container or drug cartridge, a forward chamber to house a spring to bias a needle holder, and internal latching formations to retain the needle holder with the spring compressed in the forward chamber until automatic retraction when the latching formations are released by end of plunger movement. The patent discloses that the sealing between the plunger and the body is accomplished by an over-sized plunger head that forces head and wall deformation. The disclosed spring has seals at both ends for the forward chamber. The patent teaches that the needle, its holder, spring and seals can be installed using a sliding guide. In using a syringe produced using this disclosure, the practitioner would need to exercise care when drawing and expelling a fluid during filling, because the retraction of the needle is activated by depressing the plunger sufficiently to engage cooperating latches. The engagement occurs at the bottom of the stroke to expel fluid from the syringe.

U.S. Pat. No. 5,769,822 discloses a non-reusable syringe with a hollow plunger that has a seal member thereon. The position of the plunger and the seal relative to the barrel permits the plunger, with sufficient strength, to carry applied pressure through the device during injection of a fluid and yet permit the seal disposed at one end of the plunger to have maximum sealing integrity between the plunger and a cylindrical barrel disposed around the exterior of the plunger to abate leakage of the liquid in a chamber within the barrel, as the plunger is manipulated from an expanded position to and expended position and thereafter to a third or collapsed position.

U.S. Pat. No. 6,010,486 discloses a retracting needle syringe that substantially prevents reuse of the syringe by destroying the plunger rod and the needle hub and additionally, retracts the needle into the plunger rod. The disclosed syringe includes provisions that upon fully depressing the plunger rod and applying distally directed axial force, a frangible portion of the inner hub is broken and the plunger tip dislodges to allow a spring to urge a cutter to open the chamber inside the plunger.

Most of the devices discussed in the above referenced disclosures are somewhat complex, and many require manufacture and assembly of parts with potentially difficult assembly or tight tolerance requirements. Many of the designs depend upon a careful application of forces by the practitioner to draw and expel fluids from the syringe. Also, if the tolerances between the multiple components of the device are not carefully adhered to during manufacture and assembly, normal usage may result in premature activation of the retraction function of the syringe. Current conventional syringes are considered by users to be virtually fault-free and reliable. They are used for a variety of different procedures involving both "one-shot" fill and inject procedures, as well as more complex mixing measuring and delivery functions. In order for a retractable syringe to displace these functional, utilitarian and reliable conventional syringes, the retractable syringe should not significantly interfere with the users current practices, it needs to be substantially reliable and their cost should not be prohibitive. Current conventional syringes are often manufactured at rates of several hundred per minute and their cost is generally not a significant factor in their usage. Additionally every year, hundreds of millions of small capacity (one milliliter) syringes are used outside of the normal controlled health care environment by diabetics and other self-injectors who must daily accurately inject small amounts, often only a few tenths of a milliliter. These small capacity syringes are physically quite small, with an overall length of less than five inches and an inside bore diameter of less than one-quarter inch. Reviewing the disclosures above, one skilled in the art of high volume manufacturing recognizes that assembling hundreds of millions of most of these relatively complex devices with their retraction elements contained in such a small space as a one-quarter inch diameter bore is a daunting task. Additionally, many of the disclosed devices have substantial undeliverable "dead volumes" that substantially confound many diabetics' need for accurate measuring, mixing of more than one type of insulin in the syringe and delivering small doses of insulin. The need thus exists for a selectively retractable syringe that is compatible with a small capacity syringe, that is capable of being manufactured at high volumes and is sufficiently non-complex to be reliable in use when produced at volumes of hundreds of millions per year. Such a device is disclosed herein below.

SUMMARY

A hypodermic syringe with a selectively retractable needle of the present invention includes an elongate barrel with an open proximal end, an open distal end defining a receiver and a hollow bore therethrough extending from the proximal end to the distal end. The syringe of the invention has an elongate plunger with a distal end that has an elongate first portion extending proximally therefrom and a proximal end with a second portion extending distally therefrom. The second portion has an elongate cavity therewithin with an inside diameter open to the proximal end. The plunger is disposed and sized to fit within the bore of the barrel for a slidable movement to define a chamber for receiving and expelling fluids. The inside diameter of the elongate cavity in the plunger is sufficient to accept telescopically at least a part of the first portion of the plunger. The second portion and the first portion are joined at an attachment to form a shoulder extending outwardly from the first portion, with the plunger being telescopically collapsible by movement of the second portion into the elongate cavity by an application of sufficient distal force, greater than a force required to expelled fluid from the chamber, to frangibly disrupt the attachment. The syringe of the invention further includes an elongate sleeve that is sized to fit over the first portion of the plunger and extend from the shoulder to a distance from the distal end of the plunger. The distal end of the plunger includes a stopper sized to form a slidably substantially fluid tight seal with the bore of the barrel to form the chamber. The sleeve has a cutting surface at a distal end that is disposed inside of the resilient stopper to the distance from the proximal end of the plunger. The syringe of the invention further includes an elongate hub with a proximal flange disposed within and sized for slidable movement within the receiver at the distal end of the barrel. The proximal flange defines a distal end of the chamber in the barrel. There is a passageway through the hub. The syringe has an elongate needle with a fluid path therethrough. The needle has a pointed distal end and a proximal end that is mounted in the passageway of the hub so that when the hub is disposed within the receiver at the distal end of the barrel, the pointed end of the needle extends distally outwardly and the fluid path of the needle is in fluid communication with the chamber of the barrel. There is an elongate spring disposed about the hub compressed between the receiver and the flange to provide a bias. Thus, when sufficient distal force is applied to the second portion to thereby telescopically collapse the plunger at least the distance from the cutting surface to the proximal end of the plunger, the cutting surface of the sleeve cuts through the stopper and through the flange of the hub. When the flange is cut, the hub is released from the receiver and the bias of the spring urges a sufficient movement of the hub into the chamber of the barrel to retract the needle to a position within the syringe where inadvertent contact with the pointed distal end is substantially prevented.

The syringe of the invention has an undeliverable "deadspace" volume substantially similar to conventional syringes, i.e., substantially no undeliverable volume. The syringe of the invention is as suitable for use in drawing, measuring, mixing and delivering small volumes of medicaments as conventional syringes. Unlike many of the devices disclosed above, the syringe of the invention is substantially unlikely to be inadvertently retracted by a user following currently used practices and procedures. The syringe of the invention does not depend on a user having to exercise substantially more care than with a conventional syringe when drawing and mixing fluids in the syringe to avoid inadvertent activation, and importantly, the syringe of the invention is compatible with the efficiency of high volume automated manufacture that utilizes much existing manufacturing equipment. Once needle is retracted in the syringe of the invention, the syringe cannot be restored to functionality, as the hub flange is cut through and the stopper is cut through rendering the syringe substantially unusable and protecting the needle point from inadvertent contact by anyone.

DETAILED DESCRIPTION

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents. In this disclosure, a convention is followed wherein the distal end of the device is the end closest to a patient and the proximal end of the device is the end away from the patient and closest to a practitioner.

Referring to FIGS. 1–11, a hypodermic syringe 10 of the invention includes an elongate barrel 12 with an open proximal end 14 and an open distal end 16 defining a receiver 18. Syringe 10 has a hollow bore 20 therethrough extending from proximal end 14 to distal end 16. Syringe 10 has an elongate plunger 22 with a distal end 24 that has an elongate first portion 26 extending proximally therefrom and a proximal end 30 with a second portion 32 extending distally therefrom. Second portion 32 has an elongate cavity 34 therewithin with an inside diameter "d" open to proximal end 30. Plunger 22 is sized to fit within bore 20 of the barrel for a slidable movement to define a chamber 36 for receiving and expelling fluids when disposed in bore 20. Inside diameter "d", best seen in FIG. 3, of elongate cavity 34 in second portion 32 of plunger 22 is sufficient to accept telescopically at least a part of first portion 26 of the plunger. Second portion 32 and first portion 26 are joined at an attachment 38 to form a shoulder 40 extending outwardly from first portion 26, with plunger 22 being telescopically collapsible by movement of first portion 26 into the elongate cavity by an application of sufficient distal force, greater than a force required to expel fluid from chamber 36, to frangibly disrupt attachment 38. Syringe 10 of the invention further includes an elongate sleeve 42 that is sized to fit over first portion 26 of the plunger and extend from shoulder 40 to a distance from distal end 24 of plunger 22. Distal end 24 of the plunger includes a stopper 44 sized to form a slidable substantially fluid tight seal with bore 20 of the barrel to form chamber 36. Sleeve 42 has a cutting surface 46 at a distal end 48 that is disposed inside of stopper 44 to the distance from the distal end of the plunger. Syringe 10 of the invention further includes an elongate hub 50 with a proximal flange 52 disposed within and sized for slidable movement within receiver 18 at distal end 16 of the barrel. Proximal flange 52 defines a distal end of chamber 36 in barrel 12. There is a passageway 54 through hub 50. Syringe 10 has an elongate needle 56 with a fluid path 58 therethrough. Needle 56 has a pointed distal end 60 and a proximal end 62 that is mounted in passageway 54 of hub 50 so that when hub 50 is disposed within receiver 18 at the distal end of barrel 12, pointed end 60 of the needle extends distally outwardly and fluid path 58 of needle 56 is in fluid communication with chamber 36 of barrel 12. There is an elongate spring 64 disposed about hub 50, compressed between a inward step 19 on receiver 18 and flange 52 to provide a bias. Thus, when sufficient distal force is applied to plunger 22 to frangibly disrupt attachment 38 between first portion 26 and second portion to thereby telescopically collapse first portion into cavity 34 of second portion thereby telescopically collapse the plunger at least the distance from cutting surface 46 to the proximal end of the plunger. The applied force causes cutting surface 46 of the sleeve 42 to cut through plunger 44 and through flange 52 of the hub. When flange 52 is cut, hub 50 is released from receiver 18 and the bias of spring 64 urges a sufficient movement of hub 50 to retract needle 56 to a position within syringe 10 where inadvertent contact with pointed distal end 60 is substantially prevented. Additionally, by cutting through plunger 44, flange 52 and withdrawal of needle 56, syringe 10 is rendered substantially permanently non-functional.

Figure 3:
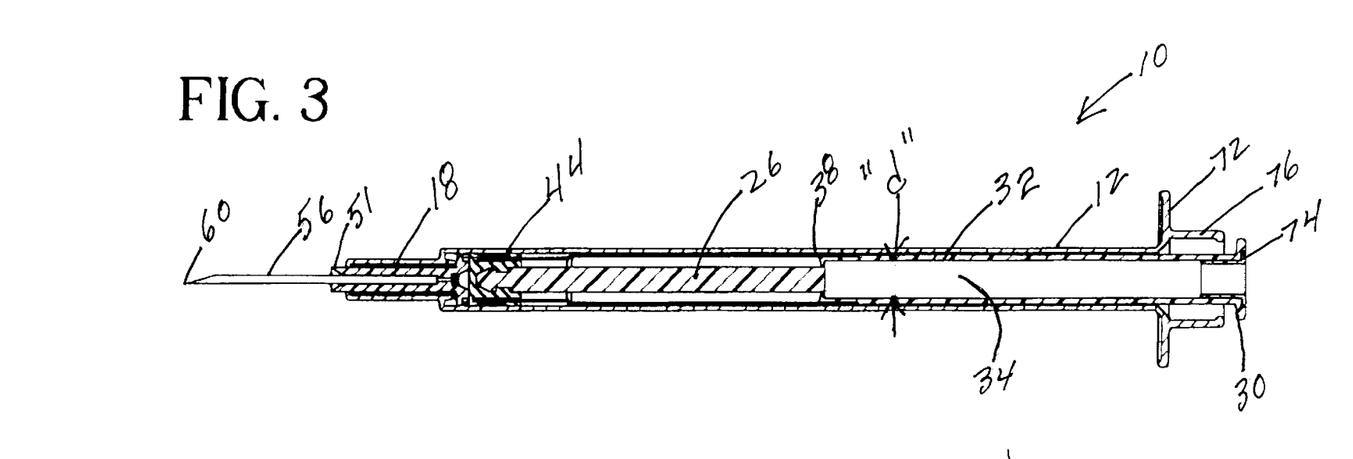
FIG. 3 is a cross-sectional view of the syringe of FIG. 2 taken along the line 3—3.

Referring to FIGS. 3–9, the sequence of the use and retraction of the needle is illustrated. FIG. 3, a cross-sectional view of the syringe of the invention is shown. In a preferred embodiment, this syringe is similar in appearance, physical size, capacity and function to a conventional one-milliliter syringe. In one embodiment, this preferred one-milliliter syringe is calibrated in units of insulin, 100 units being one milliliter. These one-milliliter syringes are physically quite small, with an overall length of less than five inches and an inside bore diameter of less than one-quarter inch. Millions of these syringes are used daily, mostly in non-clinical settings by individual users. Syringe 10 of the invention may be used by these individual users in similar fashion to the widely used current conventional syringes to draw, mix and inject insulin. For other applications, the syringe of the invention may be produced in many other sizes, calibrations and capacities that are considered as within the scope of the present invention.

Figure 3A:
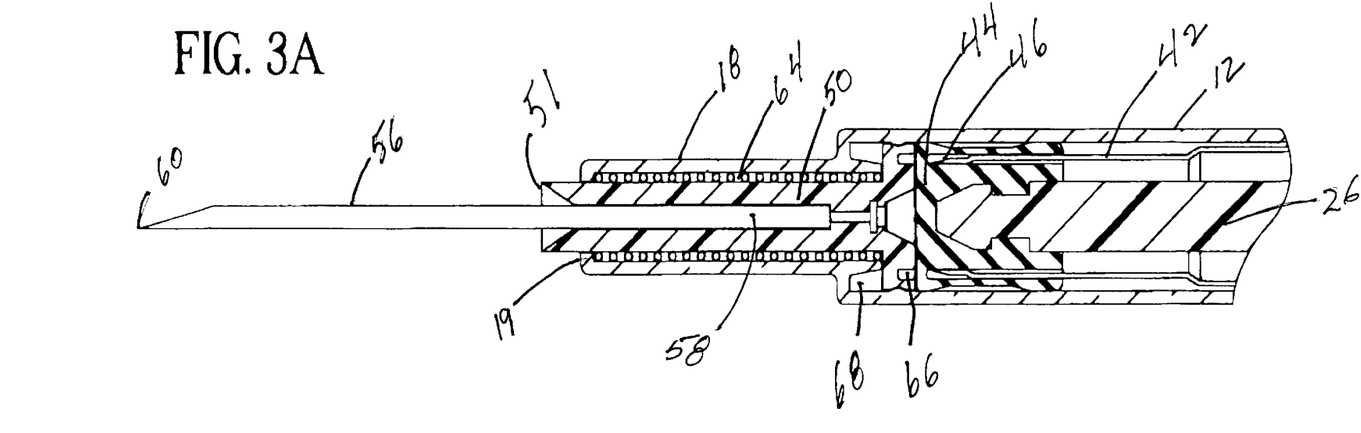
FIG. 3a is an enlarged cross-sectional view of a portion of the syringe of FIG. 3, with the plunger at the distal position in the chamber.
Figure 4:
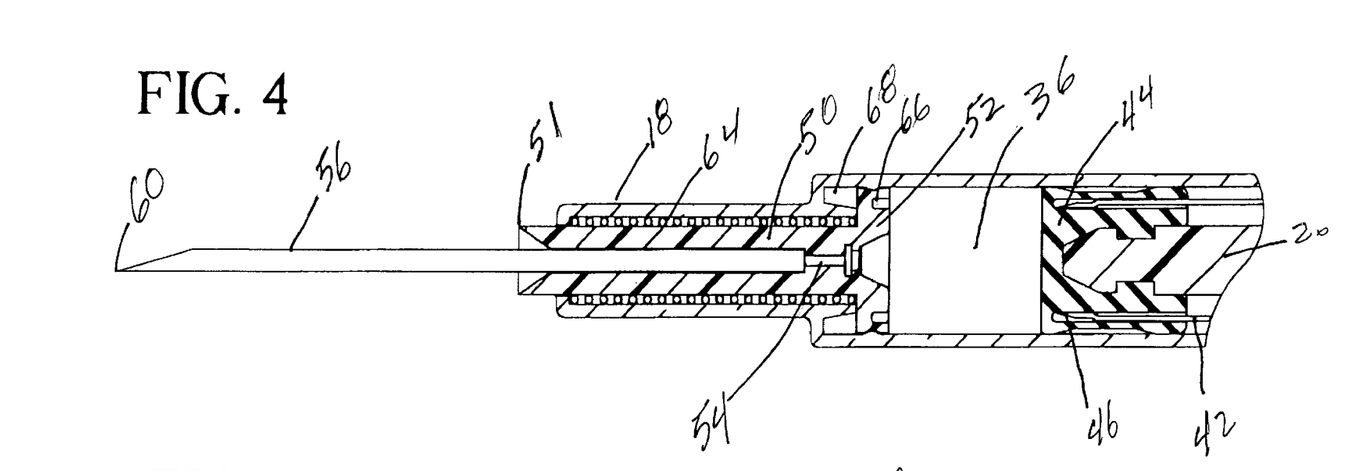
FIG. 4 is a cross-sectional view, analogous to FIG. 3a, with the plunger withdrawn a distance proximally.
Figure 5:
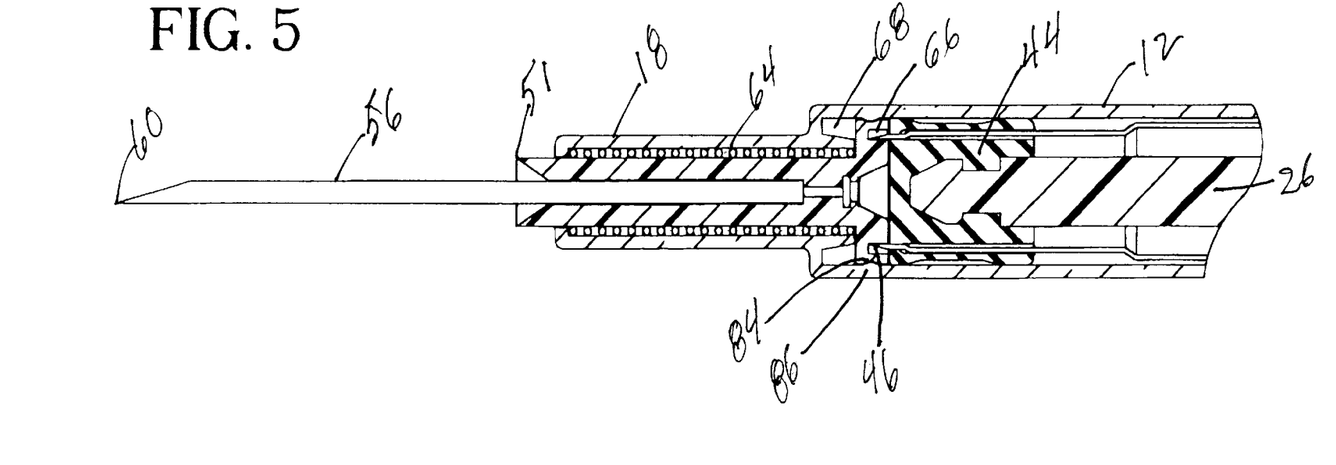
FIG. 5 is a cross-sectional view, analogous to FIG. 3a, with the plunger depressed sufficiently distally to initiate a retraction process.
Figure 6:
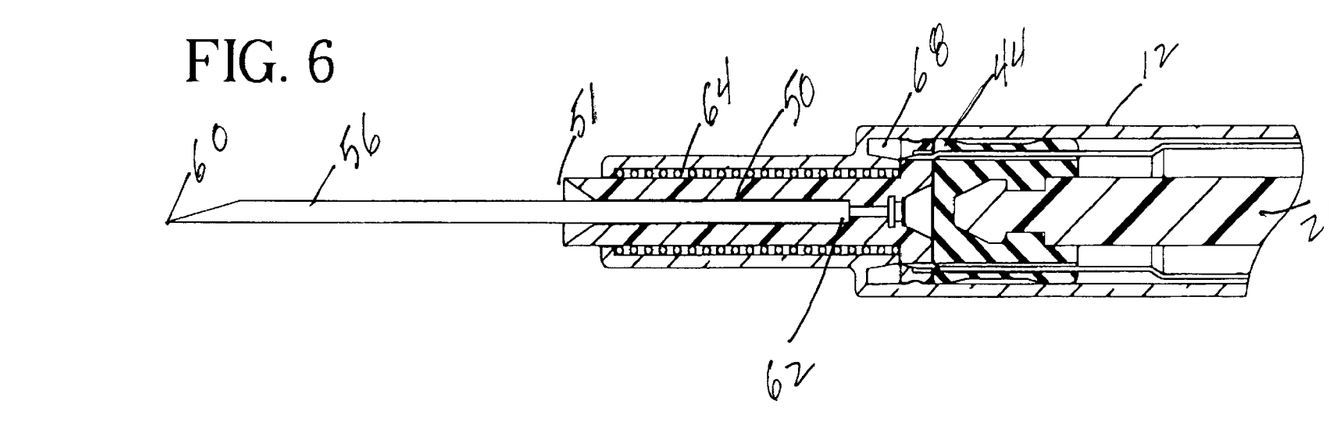
FIG. 6 is a cross-sectional view, analogous to FIG. 3a, with the plunger depressed sufficiently to continue the retraction process illustrated in FIG. 6.
Figure 7:
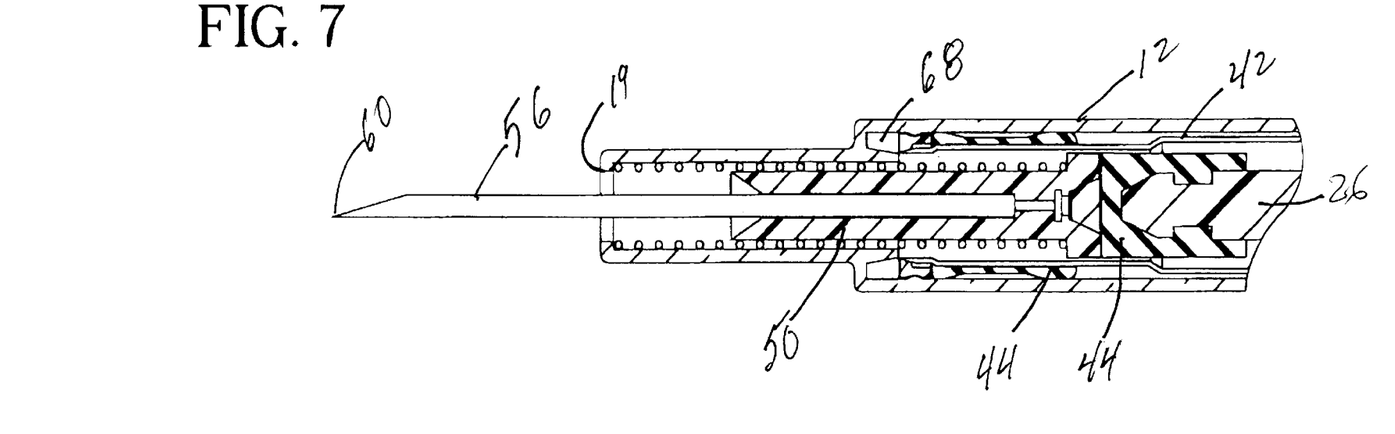
FIG. 7 is a cross-sectional view, analogous to FIG. 3a, with the retraction process partially completed.
Figure 8:
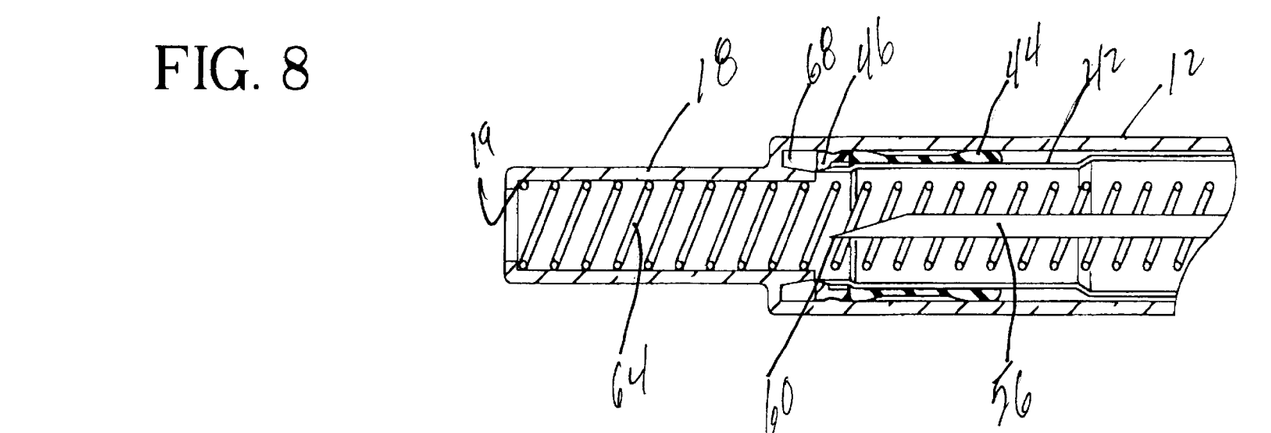
FIG. 8 is a cross-sectional view, analogous to FIG. 3a, with the retraction process substantially complete.
Figure 9:
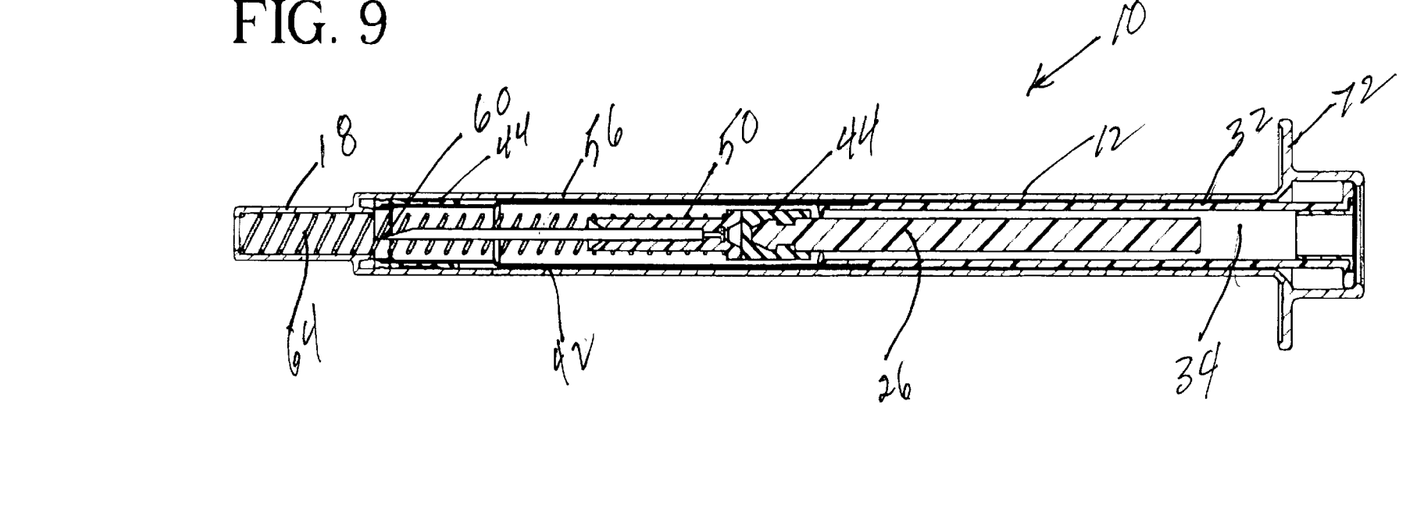
FIG. 9 is a cross-sectional view, analogous to FIG. 3, with the retraction process substantially complete.

FIGS. 3a and 4 are enlargements of the distal end of the barrel showing the details of the needle retraction mechanism with plunger stopper 44 being at and withdrawn from the distal end of chamber 36 to draw and to expel fluid from the chamber. FIG. 5 shows the effect of application of a distal force to plunger 22 beyond that force necessary to expel fluid from chamber 36. When attachment 38 is disrupted, best seen in FIGS. 3 and 9, first portion 26 telescopically collapses into cavity 34 of second portion 32. When this collapse occurs, cutting surface 46 at distal end 48 of sleeve 48 cuts through stopper 44. Flange 52 preferably includes a recess 66 to allow stopper 44 to be stretched by cutting surface 46 as the stopper is cut. Additionally, as seen in FIG. 7, recess 66 provides an area of reduced thickness in flange 50 so that as the distal force is continued, flange 50 is cut through, cutting surface 46 enters a depression 68 in receiver 18 and flange 50 is released so that spring 64 can urge movement of the hub proximally to withdraw needle 56 to the position, best seen in FIGS. 8 and 9 where pointed distal end 60 is substantially protected from inadvertent exposure. Referring to FIG. 9, one can see that when plunger 22 is fully depressed, distal end 48 of sleeve 42 is distal in barrel 12 and first portion 26 is contained substantially within cavity 34 of second portion 26.

Figure 11:
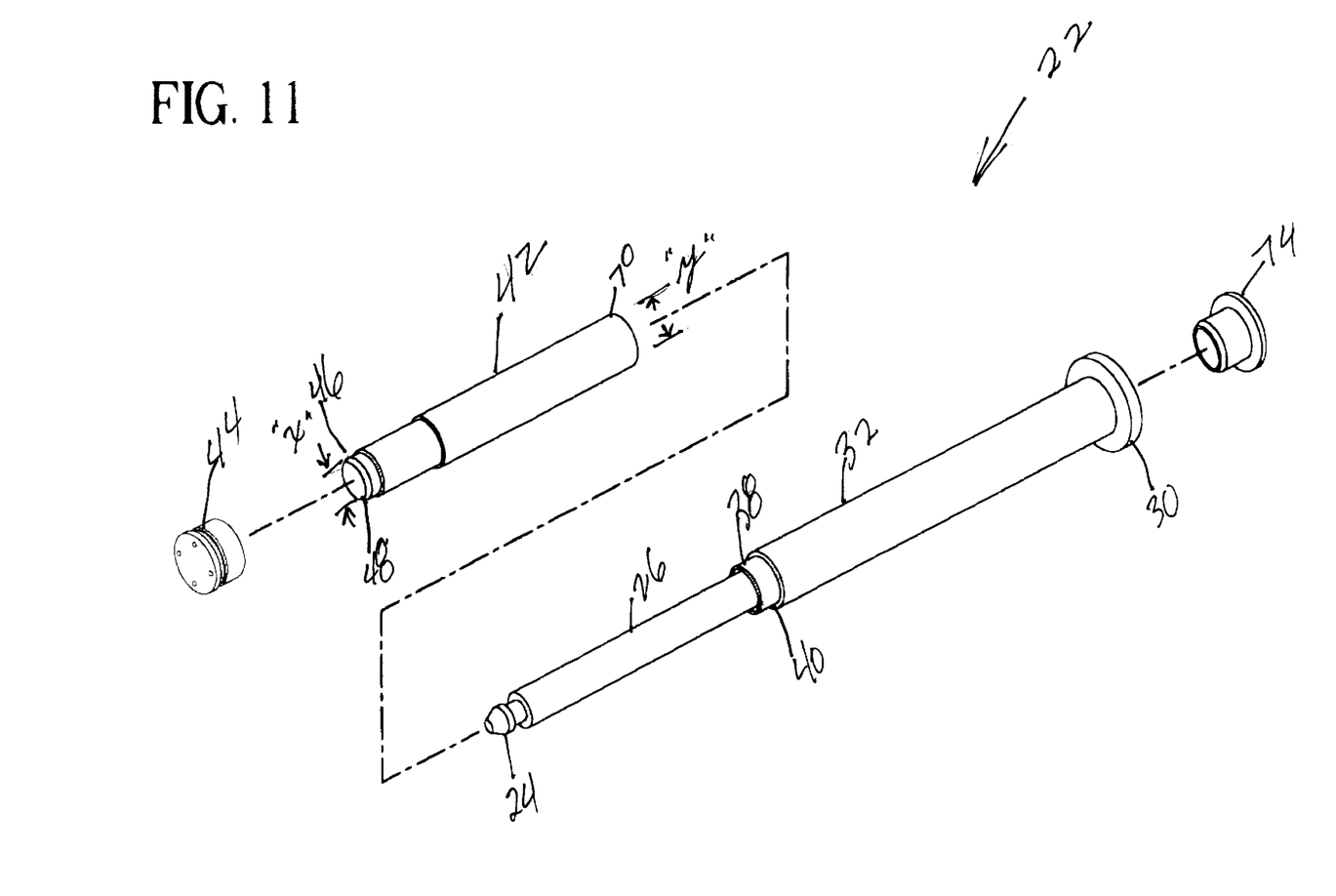
FIG. 11 is an exploded perspective view of the plunger of the syringe of FIG. 1.

Preferably, sleeve 42 is formed from a metallic material such as stainless steel or the like, and formed into the desired shape by a deep drawing process. Following the forming, the sleeve is subjected to an electrochemical finishing process that sharpens cutting surface 46 as well as cleaning and polishing the inside and the outside of the sleeve. Other methods of forming including, but not limited to, stamping, machining, powdered metal sintering and the like, are used for forming parts similar to sleeve 42 and operations such as grinding, thermally treating, honing and stropping are also useful for forming cutting surface 46 and are considered within the scope of the invention. Referring to FIG. 11, preferably, a diameter "x" of distal end 48 of sleeve 42 is smaller than a diameter "y" at a proximal end 70 where sleeve 42 is mounted on shoulder 40 of plunger 22. Plunger 22 preferably includes a plug 74 at proximal end 30 to close cavity 34 at the proximal end of the plunger. Attachment 38 of first portion 26 to second portion 32 is preferably formed as a section with a reduced thickness as compared to a wall thickness of cavity 34 of second portion 32. Preferably, plunger 22 is formed by an injection molding process, a process that allows control of the wall thickness. Plunger 22 preferably is formed from a thermoplastic material such as polypropylene, filled polypropylene, polystyrene, filled polystyrene polyethylene and the like.

Figure 1:
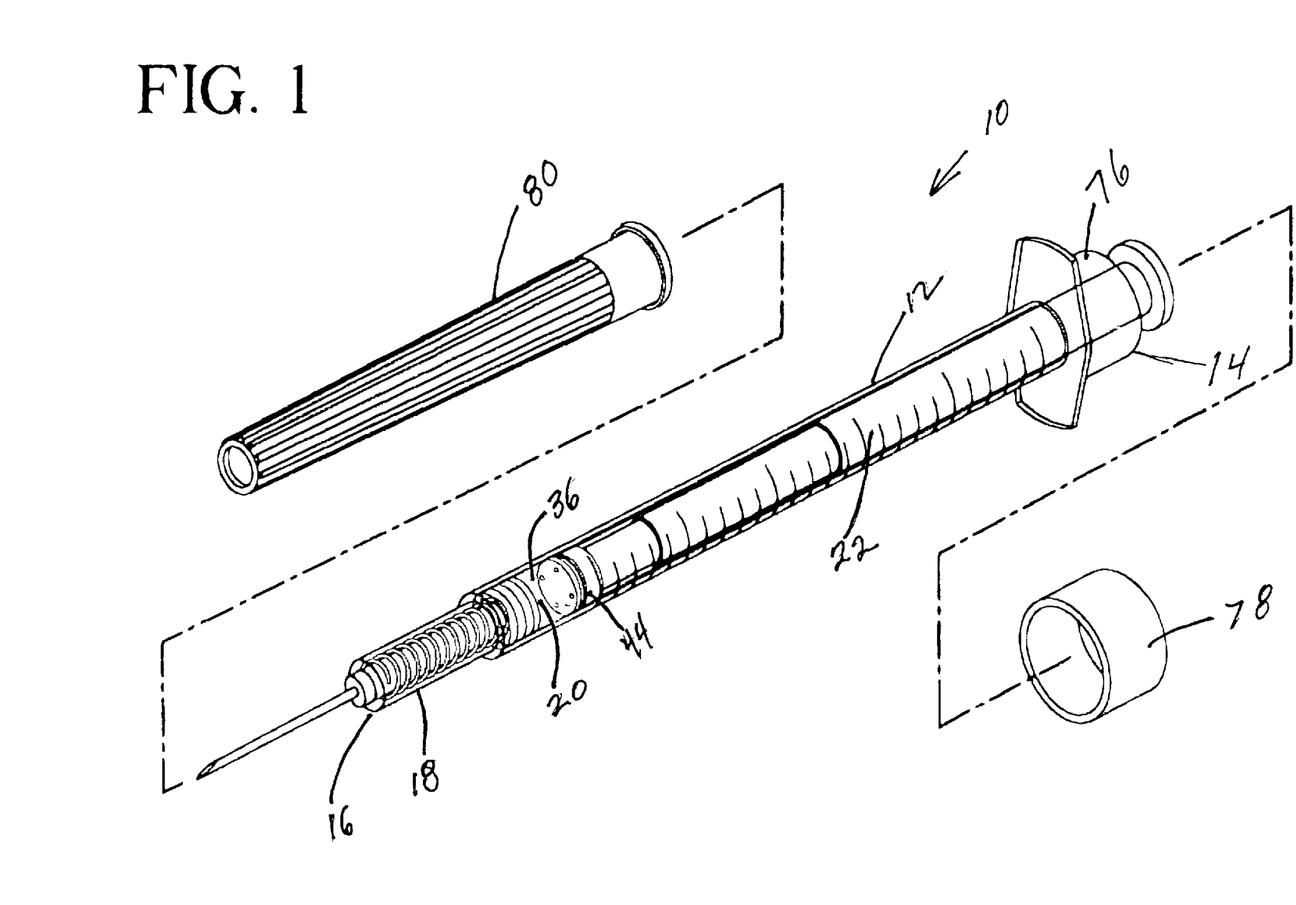
FIG. 1 is a partially exploded perspective view of the syringe of the invention.
Figure 2:
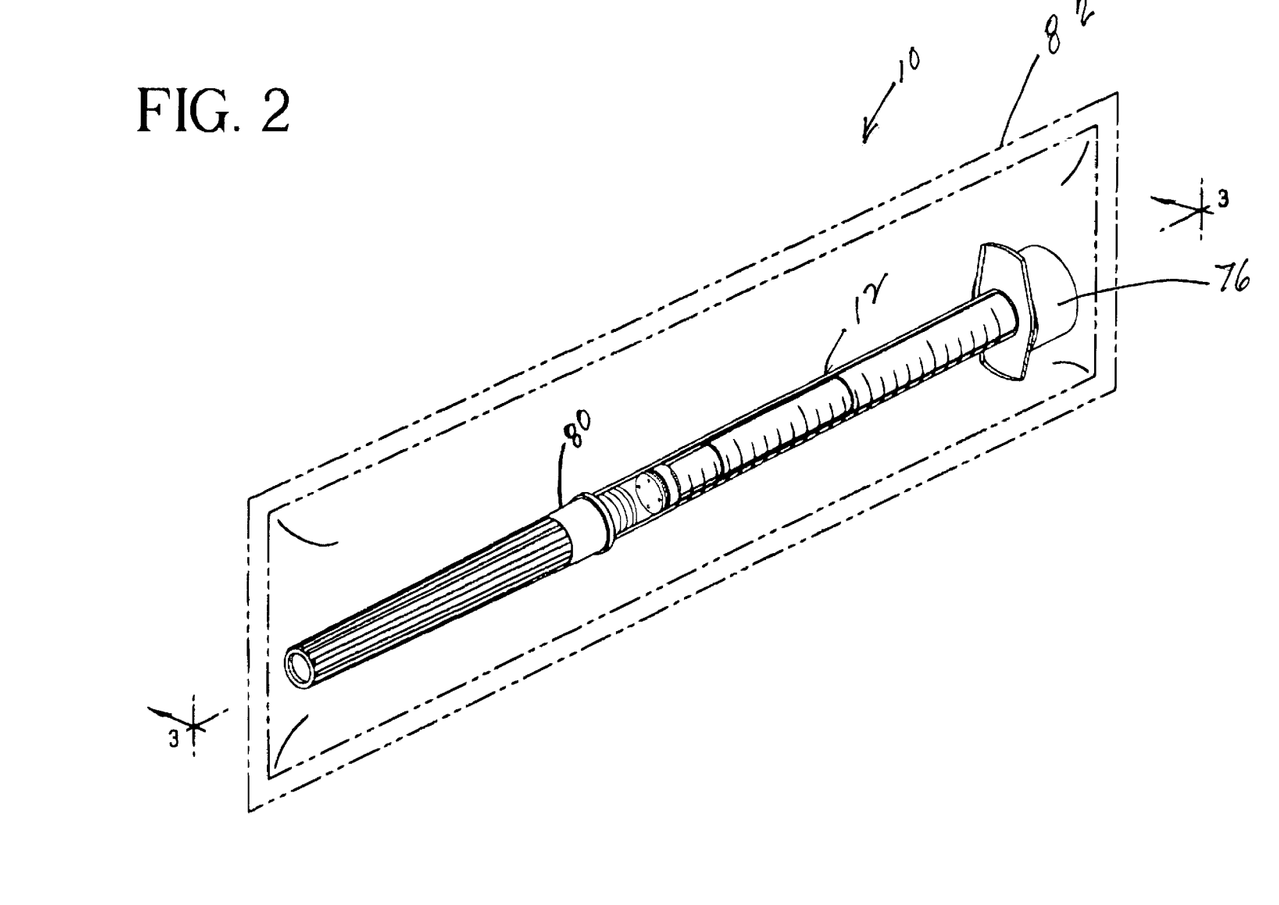
FIG. 2 is a perspective view of the syringe of FIG. 1 sealed in a package.

As seen in FIGS. 1 and 2, syringe 10 of the invention preferably has a finger press 72 at proximal end 16 of barrel 12 that includes a collar 76 to receive a removable cap 78 to enclose the proximal end of the plunger. Preferably, receiver 18 is shaped to receive a removable shield 80 to protect needle 56 from damage prior to use. Preferably, cap 78 and shield 80 are designed so that when the cap and shield are positioned on syringe 10, passage of microorganisms is substantially prevented. Preferably, once the cap and shield are in place, syringe 10 is exposed to conditions that render any microorganisms in the fluid path of the syringe substantially non-viable. The placement of the cap and shield provide a closed package for the fluid path of syringe 10 and provide a "self-contained" sterile package. Preferably, cap 78 and shield 80 are frangibly attached to syringe 10, so that once the cap and shield are position, they cannot be removed without disruption of the frangible attachment thus providing the user with an indication of tamper-evidence that the syringe has not previously been used. Alternatively, syringe 10 may be placed in a package 82, best seen in FIG. 2, that is formed from materials substantially resistant to the passage of microorganisms. In either case, suitable conditions for rendering microorganisms substantially non-viable include, but are not limited to, exposure to ionizing radiation, chemical sterilants and the like. Suitable ionizing radiation is provided by electron beam, gamma radiation and ultra-violet sources. Suitable chemical sterilants include ethylene oxide, vapor phase hydrogen peroxide and the like. When selecting materials for forming syringe 10, consideration must be given to the method of sterilization to ensure that the materials are compatible with the method selected. Once exposed to the conditions that render microorganisms non-viable, syringe 10 is considered to be "sterile" until cap 78 and shield 80 are removed or package 82 is opened.

Figure 10:
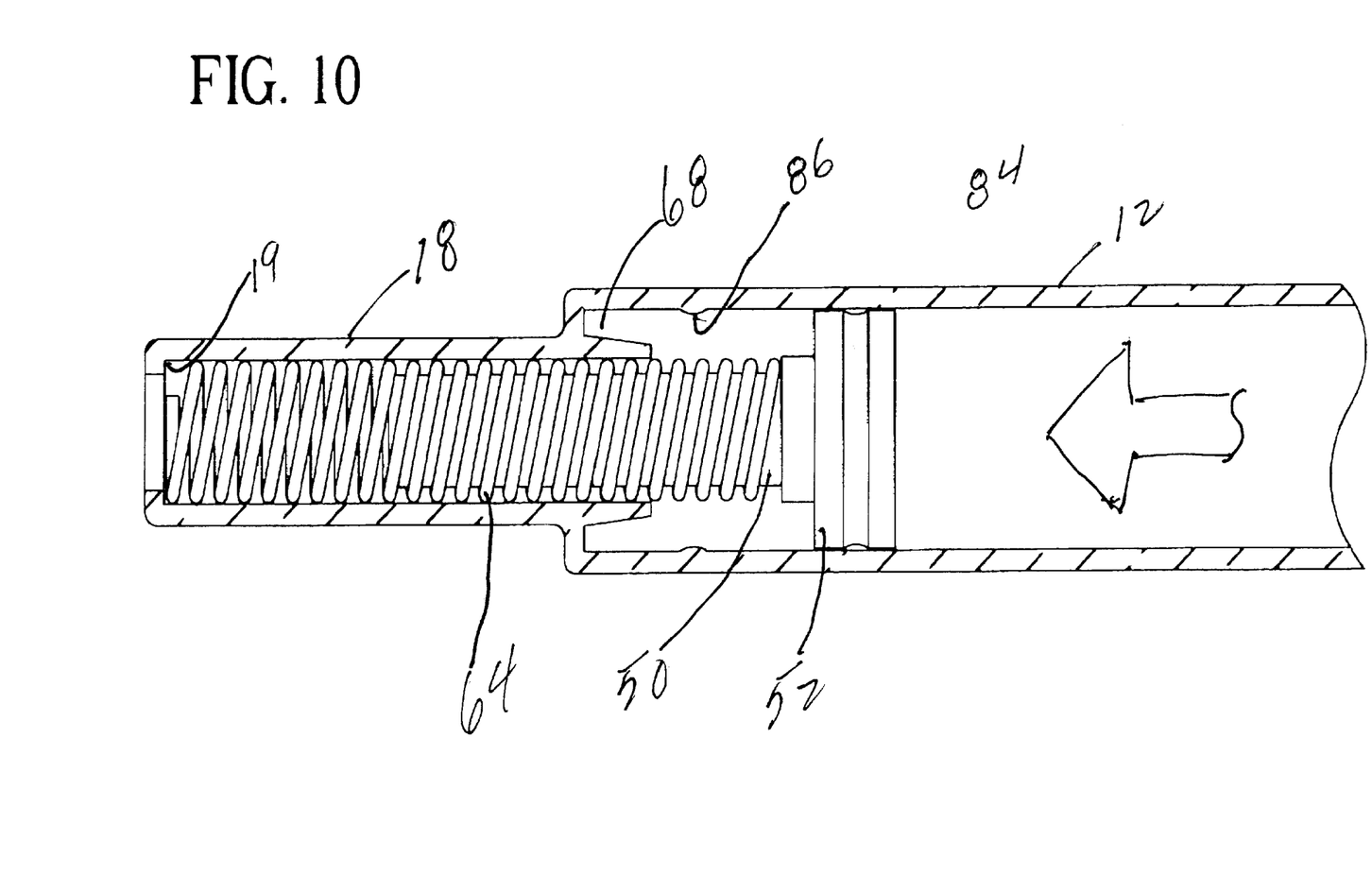
FIG. 10 is a cross-sectional view of the spring and hub during assembly into the barrel of the syringe.

A method for assembling retractable needle syringe 10 is illustrated in FIG. 10, an assembly including hub 50 and spring 64 is put together by placing spring 64 over hub 50 to engage flange 52. This assembly is then introduced, see FIG. 10, into open proximal end 14 of barrel 12 and moved distally through bore 20 to a position where a void 84 on flange 52 engages an at least one inward projection 86 on the inside surface of bore 20. When flange 52 is positioned so that void 84 engages inward projection 86, hub 50 is retained in barrel 12, spring 64 is in a compressed state between flange 52 and inward step 19. A distal end 51 of hub 50 is then available to receive needle 56 using conventional cannulation apparatus. Preferably, as shown in the Figs., distal end 51 of the hub projects beyond step 19 of the receiver. Alternatively, for particular applications, it may be preferred that distal end 51 be substantially flush with step 19 of receiver 18 and as such is considered within the scope of the present invention. The needle cannulation process preferably includes application of a preselected amount of an adhesive adjacent to proximal end 62 of the needle and positioning the needle in passageway 54 of hub 50 so that sharpened end 60 projects distally outwardly and fluid path 58 of the needle is in fluid communication with chamber 36 of the barrel. The adhesive serves to bond needle 56 into hub 50. Once needle 56 is positioned and bonded into hub 50, a lubricant may be applied to the needle using the same equipment used for conventional non-retractable fixed needle syringes.

The retractable needle syringe of the invention is simple to manufacture and assemble, is compatible with much current manufacturing equipment and is usable in substantially the same ways as conventional syringes. The syringe of the invention, unlike previously disclosed retractable needle syringes, is compatible with high speed maufacturing requirements of small size syringes and is unlikely to be inadvertently activated by normal usage.

What is claimed is:

1. A hypodermic syringe with a selectively retractable needle comprises;

an elongate barrel having an open proximal end and a distal end defining a receiver, said barrel having a hollow bore therethrough extending from said proximal end to said distal end;

an elongate plunger having a distal end with an elongate first portion extending proximally therefrom and a proximal end with a second portion extending distally therefrom, said second portion having an elongate cavity therewithin with an inside diameter open to said proximal end, said plunger being sized to fit within said bore of said barrel for a slidable movement to define a chamber for receiving and expelling fluids, said inside diameter of said elongate cavity in said plunger being sufficient to accept telescopically at least a part of said first portion of said plunger, said second portion and said first portion being joined at an attachment to form a shoulder extending outwardly from said first portion, said plunger being telescopically collapsible by movement of said first portion into said elongate cavity by an application of sufficient distal force, greater than a force required to expelled fluid from said chamber, to frangibly disrupt said attachment of said first portion to said second portion;

an elongate sleeve having a proximal end and a distal end, said proximal end being sized to fit over at least part of said first portion of said plunger and extend distally from said shoulder, said distal end of said plunger including a stopper sized to form a slidably substantially fluid tight seal with said bore of said barrel for forming said chamber, said sleeve having a cutting surface at said distal end being disposed inside of said stopper proximally from said distal end of said plunger;

an elongate hub with a proximal flange, said hub disposed within and sized for slidable movement within said receiver at said distal end of said barrel with said proximal flange defining a distal end of said chamber in said barrel, said hub having a passageway therethrough;

an elongate needle having a fluid path therethrough, said needle having a pointed distal end and a proximal end mounted in said passageway of said hub so that when said hub is disposed within said receiver at said distal end of said barrel, said pointed end of said needle extends distally outwardly and said fluid path of said needle is in fluid communication with said chamber of said barrel;

an elongate spring disposed about said hub compressed between said receiver and said flange to provide a bias, so that when a sufficient distal force, greater than the force needed to expel fluid from said chamber, is applied to said plunger to frangibly disrupt said attachment between said first portion and said second portion to thereby telescopically collapse said first portion into said second portion, and wherein said cutting surface of said sleeve cuts through said stopper and through said flange of said hub thereby to release said hub from said receiver and to allow said bias of said spring to urge a sufficient movement of said hub to a position within said syringe where inadvertent contact with said pointed distal end is substantially prevented.

2. The retractable needle syringe of claim 1 wherein said receiver is sized so that said open distal end of said barrel defining said receiver is sized and shaped to allow a slidable movement of said hub while retaining said spring about said hub.

3. The retractable needle syringe of claim 2 wherein said hub further includes a recess disposed to receive said cutting surface of said sleeve when said sleeve cuts through said stopper, thereby to facilitate a stretching of said stopper as said sleeve cuts therethrough.

4. The retractable needle syringe of claim 1 wherein said receiver further includes a depression substantially aligned with said recess in said hub disposed to receive said cutting surface of said sleeve when said sleeve cuts through said hub, thereby to facilitate said release of said hub from said receiver.

5. The retractable needle syringe of claim 1 further comprising said sleeve having a proximal diameter and a distal diameter and wherein said proximal diameter is larger than said distal diameter, thereby facilitating movement of said stopper, said hub, and said needle into said syringe.

6. The retractable needle syringe of claim 5 wherein said sleeve is formed from a metallic material.

7. The retractable needle syringe of claim 6 wherein said sleeve is subjected to an electrochemical treatment thereby enhancing said cutting surface's sharpness properties.

8. The retractable needle syringe of claim 6 wherein said metallic material is stainless steel.

9. The retractable needle syringe of claim 1 wherein said proximal end of said barrel further comprises a finger flange for assisting a practitioner's grip of said syringe during a use.

10. The retractable needle syringe of claim 9 wherein said finger flange includes a collar projecting proximally a sufficient distance, said collar being disposed and shaped to receive a removable for covering said plunger and wherein said receiver at said distal end of said barrel is shaped to receive a removable shield for protecting said distal point of said needle.

11. The retractable needle syringe of claim 10 wherein said distal point of said needle is formed into a sharpened point to facilitate a penetration of said needle into a patient's tissue.

12. The retractable needle syringe of claim 10 wherein said cap disposed on said collar and said shield disposed on said receiver are sufficient to substantially prevent passage of microorganisms beyond said cap and shield, and wherein said syringe is exposed to conditions that substantially render any microorganisms therein substantially non-viable.

13. The retractable needle syringe of claim 12 wherein said cap and said shield are each provided with a frangible attachment, so that neither said cap nor said shield are removable from said collar and said receiver respectively without disruption of said attachments, thereby providing a positive evidence to the practitioner that once said cap and said shield are positioned on said collar and said receiver, they have not been removed prior to the intended use, thereby providing a "tamper-evidence".

14. The retractable needle syringe of claim 1 wherein said spring is formed from a metallic material.

15. The retractable syringe of claim 1 wherein said elongate plunger further comprises said second portion having said cavity therein includes a wall having a wall thicknessness and said attachment of said first portion and said second portion to form said shoulder comprises an area of reduced thicknessness compared to said wall thicknessness of said second portion, so that when said force greater than the force required to expel fluid from said chamber is applied to said plunger, said area of reduced thicknessness is frangibly disrupted, breaking said attachment of said first portion to said second portion, thereby collapsing at least part of said first portion into said cavity in said second portion and allowing said cutting surface to cut through said stopper and said flange to release said hub and withdraw said needle.

16. The retractable needle syringe of claim 15 wherein said cavity in said second portion of said elongate plunger further comprises a proximal plug for closing said proximal end of said cavity.

17. The retractable needle syringe of claim 1 being placed in a package formed from materials substantially resistant to the passage of microorganisms and exposed to conditions that render any microorganisms therein substantially non-viable.

18. The retractable needle syringe of claim 1 wherein said hollow bore of said barrel has an inside surface having at least one inward projection thereon and said flange on said hub has a conjugate depression thereon so that when said hub is disposed in said receive at said distal end of said barrel with said spring compressed between said flange and said receiver, said depression engages said projection thereby retaining said hub in said barrel.

19. The retractable syringe of claim 1 wherein said barrel is formed from a thermoplastic material.

20. The retractable syringe of claim 1 wherein said stopper is formed from a resilient material selected from the group consisting of thermoset natural rubber, thermoset synthetic rubber and thermoplastic elastomer.

21. A method for assembling a retractable needle syringe comprises:
   providing an elongate barrel having an open proximal end and an open distal end defining a receiver with an inward shoulder, said barrel having a hollow bore therethrough extending from said proximal end to said distal end, said hollow bore having an inside surface with at least one inward projection thereon;
   providing an elongate hub with a proximal flange and a distal tip, said hub sized for slidable movement within said receiver at said distal end of said barrel with said flange having a depression conjugate to said inward projection, said hub having a passageway therethrough;
   placing an elongate spring about said hub to form an assembly;
   inserting said assembly into said barrel from said proximal end to a position wherein said spring is compressed between said flange and said shoulder and said depression on said flange engages said inward projection on said bore;
   providing an elongate needle having a fluid path therethrough, said needle having a pointed distal end and a proximal end;
   mounting said needle into said distal end of said hub so that said needle is connected to said passageway of said hub with said point end of said needle extending distally outwardly and said fluid path of said needle is in fluid communication with said chamber of said barrel;
   providing an elongate plunger having a distal end with an elongate first portion extending proximally therefrom and a proximal end with a second portion extending distally therefrom, said second portion having an elongate cavity therewithin with an inside diameter open to said proximal end, said proximal end being closed by a plug, said plunger being disposed and sized to fit within said bore of said barrel for a slidable movement to define a chamber for receiving and expelling fluids, said inside diameter of said elongate cavity in said plunger being sufficient to accept telescopically at least a part of said first portion of said plunger, said second portion and said first portion being joined at an attachment to form a shoulder extending outwardly from said first portion, said plunger being telescopically collapsible by movement of said first portion into said elongate cavity by an application of sufficient distal force, greater than a force required to expelled fluid from said chamber, to frangibly disrupt said attachment of said first portion to said second portion, said plunger including an elongate sleeve having a proximal end and a distal end, said proximal end being sized to fit over at least part of said first portion of said plunger and extend distally from said shoulder, said distal end of said plunger including a stopper sized to form a slidably substantially fluid tight seal with said bore of said barrel for forming said chamber, said sleeve having a cutting surface at said distal end being disposed inside of said stopper proximally from said distal end of said plunger;

placing said distal end of said plunger into said proximal end of said barrel and moving said plunger distally into said bore of said barrel thereby assembling said syringe having said retractable needle.

* * * * *